(12) United States Patent
Giorgi et al.

(10) Patent No.: US 6,780,968 B1
(45) Date of Patent: Aug. 24, 2004

(54) MONOCYCLIC COMPOUNDS WITH FOUR BIFUNCTIONAL RESIDUES HAVING NK-2 ANTAGONIST ACTION

(75) Inventors: Raffaello Giorgi, deceased, late of Pisa (IT), by Rosaria Pirari, heir, Chiara Giorgi, Gabriele Giorgi, legal representatives; Alberta Giorgi, legal representative, Milan (IT); Cristina Di Bugno, Pisa (IT); Danilo Giannotti, Altopascio (IT); Carlo Alberto Maggi, Florence (IT)

(73) Assignee: Menarini Ricerche S.p.A., Pomezia (IT)

( * ) Notice: Subject to any disclaimer, the term of this patent is extended or adjusted under 35 U.S.C. 154(b) by 0 days.

(21) Appl. No.: 09/355,210

(22) PCT Filed: Feb. 4, 1998

(86) PCT No.: PCT/EP98/00599

§ 371 (c)(1),
(2), (4) Date: Jul. 12, 2000

(87) PCT Pub. No.: WO98/34949

PCT Pub. Date: Aug. 13, 1998

(30) Foreign Application Priority Data

Feb. 7, 1997 (IT) ............................ FI97A0020

(51) Int. Cl.$^7$ ............................ C07K 7/50
(52) U.S. Cl. .................. 530/317; 530/330; 514/11; 514/18
(58) Field of Search .................. 514/11, 18; 530/317, 530/330

(56) References Cited

FOREIGN PATENT DOCUMENTS

JP          06-172385    *  6/1994
WO          9321227         10/1993

OTHER PUBLICATIONS

Rothe, M. Pept., Proc. Eur. Pept. Symp. 14th, pp. 71–78, 1976.*
Torsello, Antonio (Endocrinology 143 (5) 1968, 2002).*
McFadyen (Journal of Peptide Research (Mar. 2000) 55 (3) 255–61).*
Keith, (Molecular Pharmacology 53 (3) 377–84, 1998).*
Lunec, (Melanoma Research (May 1992) 2 (1) 5–12).*
Xiao (Biochemistry 40, 2860, 2001).*
Foster, P. S. (Clinical and Experimental Allergy 29 (1) 12–16, 1999).*
Henderson (J. Immunol. 164, 1086–95, 2000).*
Wallace J. L. (Regulatory Peptides 73 (2) 95–101, 1998).*
Fahy J. V. (American Journal of Respiratory and Critical Care Medicine 152 (3) 879–84, 1995).*
Evangelista S. (Neuropeptides 30 (5) 425–8, 1996).*
Reinshagen M. (Journal of Pharmacology and Experimental Therapeutics 286(2) 657–61, 1998).*
Girard V (European Respiratory Journal 8 (7) 1110–14, 1995).*
Biyah K (European Journal of Pharmacology 308 (3), 325–8, 1996).*
Evangelista, S. (Current Pharmaceutical Design 7(1) 19–30, 2001).*
Holzer, Peter (Current Opinion in Pharmacology 1(6) 583–590, 2001).*
Rogers, Duncan F. (Expert Opinion on Therapeutic Patents 11(7), 1097–1121, 2001).*
European Journal of Pharmacology, 241(1993) 17–25; "Tachykinin–Mediated Respiratory Effects in Conscious Guines Pigs: Modulation by NK–1 and NK–2 Receptor Antagonists", Elizabeth M. Kudlacz et al.
Psychopharmacology (1995) 121:186–191; "The Anxiolytic–like Activity of GR159897, a Non–Peptide NK–2 Receptor Antagonist, in Rodent and Primate Models of Anxiety"; D. M. Walsh et al.
Br. J. Pharmacol. (1991), 104, 355–360; "Pharmacological Specificity of Novel, Synthetic, Cyclic Peptides as Antagonists at Tachykinin Receptors"; A.T. McKnight et al.
Journal of Medicinal Chemistry, 1994, vol. 37, No. 21; "Influence of Lipophilicity on the Biological Activity of Cyclic Pseudopeptide NK–2 Receptor Antagonists"; Laura Quartara et al.

* cited by examiner

*Primary Examiner*—Christopher S. F. Low
*Assistant Examiner*—David Lukton
(74) *Attorney, Agent, or Firm*—Hedman & Costigen, P.C.

(57) ABSTRACT

Disclosed are monocyclic compounds containing four bifunctional residues linked together via peptide or pseudopeptide bonds of the general formula (I):

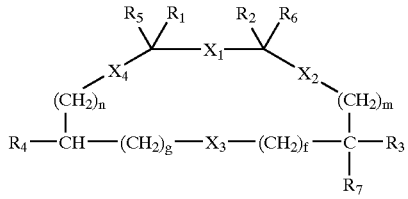

having tachykinin receptor antagonist activity. In particular, compounds of formula I are shown to be neurokinin-2 (NK-2) antagonists useful in the treatment or prevention of disorders of the central nervous system, inflammatory diseases, asthma, or pain.

13 Claims, No Drawings

MONOCYCLIC COMPOUNDS WITH FOUR BIFUNCTIONAL RESIDUES HAVING NK-2 ANTAGONIST ACTION

BACKGROUND OF THE INVENTION

The present invention refers to new compounds having the general formula (I):

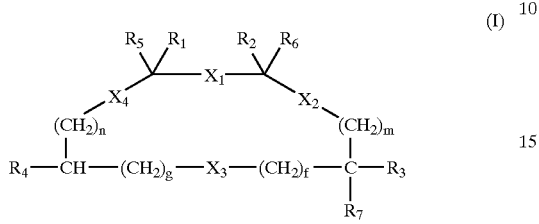

in which:

$X_1$, $X_2$, $X_3$, $X_4$, which may be the same or different from one another, represent a group chosen from among —CONR—, —NRCO—, —OCO—, —COO—, —CH$_2$NR—, —NR—CH$_2$—, CH$_2$—CH$_2$, where R is H or a $C_{1-3}$ alkyl or benzyl;

f, g, h, m, which may be the same or different from one another, represent a number chosen from among 0, 1 or 2;

$R_1$ and $R_2$, which may be the same or different from one another, represent a —(CH$_2$)$_r$—Ar group, where r=0, 1, 2 and where Ar is an aromatic group chosen from among: benzene, naphthalene, thiophene, benzothiophene, pyridine, quinoline, indole, furan, benzofuran, thiazole, benzothiazole, imidazole, and benzo-imidazole, the said Ar group being possibly substituted with a maximum of 2 residues chosen from among $C_{1-3}$ alkyl or halo-alkyl, $C_{1-3}$ alkoxyl, $C_{2-4}$ amino-alkoxyl, halogen, OH, NH$_2$, NR$_{13}$R$_{14}$ where R$_{13}$ and R$_{14}$, which may be the same or different from one another, represent hydrogen or $C_{1-3}$ alkyl;

$R_3$ represents a group chosen from among:

hydrogen linear or branched alkyl having the formula $C_nH_{2n+1}$, with n=1–5, cyclo-alkyl or alkylcyclo-alkyl groups having the formula $C_nH_{2n-1}$ with n=5–9

(CH$_2$)$_r$—Ar$_1$, where r=0, 1, 2 and where Ar$_1$ is an aromatic group chosen from among: benzene, naphthalene, thiophene, benzothiophene, pyridine, quinoline, indole, furan, benzofuran, thiazole, benzothiazole, imidazole, and benzo-imidazole, the said Ar$_1$ group being possibly substituted with a maximum of 2 residues chosen from among $C_{1-3}$ alkyl or halo-alkyl, $C_{1-3}$ alkoxyl or amino-alkoxyl, halogen, OH, NH$_2$, NR$_{13}$R$_{14}$, where R$_{13}$ and R$_{14}$, which may be the same or different from one another, represent hydrogen or $C_{1-3}$ alkyl;

$R_4$ represents a group chosen from among:

hydrogen or $C_{1-6}$ alkyl

L-Q, where L is a chemical bond or a linear or branched $C_{1-6}$ alkyl residue and Q is a group chosen from among:

i) H, OH, OR$_9$, NH$_2$, NR$_9$R$_{10}$, guanidine, sulphate, phosphonate, phosphate, where R$_9$ and R$_{10}$, which may be the same or different from one another, represent a hydrogen, $C_{1-3}$ alkyl group, $C_{1-3}$hydroxyalkyl, $C_{1-3}$dihydroxyalkyl, $C_{1-3}$alkyl-CONHR$_{12}$, $C_{1-3}$alkyltetrazole, $C_{1-3}$alkyl-COOH or wherein R$_9$R$_{10}$ joined together form with the N-atom a saturated 4–6 membered heterocycle possibly containing a further heteroatom chosen in the group consisting of N, O, S and wherein R$_{12}$ is a mono-, di-, tri-glycosidic group possibly protected with one or more $C_{1-3}$-acyl groups or substituted with amino-groups or $C_{1-3}$acylamino-groups;

ii) COOH, tetrazole, SO$_2$NH$_2$, SO$_2$NHCOOR$_8$, $_{CONHR8}$, $_{NHCOR8}$, where R$_8$ represents a linear or cyclic $C_{1-6}$ alkyl chain containing one or more polar groups chosen from among the group: OH, NH$_2$, NR$_{15}$R$_{16}$, COOH, CONHR$_{12}$, PO$_3$H, SO$_3$H, OR$_{11}$ and where R$_{15}$ and R$_{16}$, which may be the same or different from one another, represent a hydrogen or $C_{1-3}$ alkyl group, and where R$_{11}$ is a $C_{1-3}$ alkyl or $C_{2-4}$ amino-alkyl chain, R$_{12}$ is a mono-, di-, tri-glycosidic group possibly protected with one or more $C_{1-3}$acyl groups or substituted with amino-groups or $C_{1-3}$acylamino-groups or R$_{15}$R$_{16}$ joined together form with the N-atom a saturated 4–6 membered heterocycle possibly substituted with $C_{1-3}$alkyl-groups or with saturated 4–6 membered heterocycle-groups containing at least an N-atom;

iii) COOR$_{17}$, CONHR$_{12}$, OR$_{12}$ where R$_{12}$ is a mono-, di- or tri-glycoside group possibly protected with one or more $C_{1-3}$ acyl groups or substituted with amine or $C_{1-3}$ acylamine groups and R$_{17}$ is a group R$_{12}$ as above definined or a group $C_{1-3}$alkyl, $C_{1-3}$alkylphenyl, wherein the phenyl-group can be substituted with a group OH, NO$_2$, NH$_2$, CN, CH$_3$, Cl, Br;

$R_5$, $R_6$, $R_7$, which may be the same or different from one another, represent a hydrogen or $C_{1-3}$ alkyl group; with the proviso that when $R_1$ and $R_2$ are benzyl or 4-hydroxybenzyl then $R_3$ and $R_4$ are not isopropyl.

Also included in the present invention are the pharmaceutically acceptable salts, the processes for their preparation, and the pharmaceutical compositions containing them.

In view of the presence of chiral centres in the compounds of formula (I), also the individual enantiomers and their mixtures, both in the racemic form and in the non-racemic form, form part of the present invention.

DESCRIPTION OF THE RELATED ART

The NK-2 receptor of tachykinins is widely expressed in the peripheral nervous system of mammals. One of the various effects produced by the selective stimulation of the NK-2 receptor is the contraction of smooth muscle. Hence antagonists of the NK-2 receptor may be considered agents capable of controlling excessive contraction of smooth muscle in any pathological condition in which the release of tachykinins concurs in the genesis of the corresponding disorder.

In particular, the bronchospastic and inflammatory component of asthma, coughing, pulmonary irritation, intestinal spasms, spasms of the biliary tract, local spasms of the bladder and of the ureter during cystitis, kidney infections and colics may be considered conditions in which the administration of NK-2 antagonists may be effective (E. M. Kudlacz et al., Eur. J. Pharmacol., 1993, 241, 17–25).

In addition, a number of NK-2 antagonists capable of surmounting the haemato-encephalic barrier have shown anxiolytic properties (D. M. Walsh et al., Psychopharmacology, 1995, 121, 186–191).

Cyclic compounds, and in particular cyclic hexapeptides (A. T. McKnight et al., Br. J. Pharmacol., 1991, 104, 355)

and bicyclic hexapeptides (V. Pavone et al., WO 93/212227) or cyclic hexapseudopeptides (L. Quartara et al., J. Med. Chem., 1994, 37, 3630; S. L. Harbeson et al., Peptides, Chemistry and Biology, Proceedings of the Twelfth American Peptide Symposium, 1992, 124) are known in the literature for their antagonistic activity towards the NK-2 receptor of tachykinins. In EP-A-333174 linear di- and tri-peptide compounds comprising the -D-Trp-Phe-moiety are described; such compounds possess tachykinin antagonism.

It has now surprisingly been found that products of lower molecular weight, monocyclic ones, containing only four bifunctional residues linked together via peptide or pseudopeptide bond, present high pharmacological activity associated to a considerable selectivity for the human NK-2 receptor, and thus are proposed as valid alternatives.

BRIEF DESCRIPTION OF THE DRAWING

FIG. 1 is a reaction scheme for the general synthesis of compounds of formula (1).

DETAILED DESCRIPTION OF THE INVENTION

The present invention therefore sets itself the aim of making available new monocyclic compounds containing four bifunctional residues linked together via peptide or pseudopeptide bonds having antagonistic action on the NK-2 receptor, with the general formula (I), as defined previously.

Also forming part of the present invention are the pharmaceutically acceptable salts, the processes for their preparation, and the pharmaceutical compositions containing them.

In view of the presence of chiral centres in the compounds of formula (I), also the individual enantiomers and their mixtures, both in the racemic form and in the non-racemic form, form part of the present invention.

According to the invention preferred compounds of general formula (I) are those in which:

f, g, h, m, which may be the same or different from one another, may be 0 or 1; $R_1$ and $R_2$, which may be the same or different from one another, represent the side chain of a natural amino acid chosen from among tryptophan, phenyl alanine, tyrosine, histidine or the side chain of a non-natural amino acid chosen in the group:

tryptophan and phenyl alanine, either mono- or di-substituted with residues chosen from among $C_{1-3}$ alkyl or halo-alkyl, $C_{1-3}$ alkoxyl or amino-alkoxyl, halogen, OH, $NH_2$, $NR_{13}R_{14}$, where $R_{13}$ and $R_{14}$, which may be the same or different from one another, represent a hydrogen or $C_{1-3}$ alkyl group;

$R_3$ represents a group chosen from among:

linear or branched alkyl having the formula $C_nH_{2n+1}$, with n=1–5 (chosen in the group consisting of methyl, ethyl, propyl, isopropyl, n-butyl, t-butyl) cycloalkyl or alkylcycloalkyl of formula $C_nH_{2n-1}$ with n=5–9 (chosen in the group consisting of cyclopentyl, cyclohexyl, methylcyclohexyl)

$(CH_2)_r$—$Ar_1$, where r=1 or 2 and where $Ar_1$ is an aromatic group chosen from among: α-naphthyl, β-naphthyl, phenyl, indole, the said $Ar_1$ group being possibly substituted with a maximum of 2 residues chosen from among $C_{1-3}$ alkyl, $CF_3$, $C_{1-3}$ alkoxyl, Cl, F, OH, $NH_2$;

$R_4$ represents an L-Q group where:

L is a chemical bond or $CH_2$, and

Q is a group chosen from among:

OH, $NH_2$, $NR_9R_{10}$, $OR_{11}$, and where $R_9$ and $R_{10}$, which may be the same or different from one another, represent a hydrogen or $C_{1-3}$ alkyl group, $C_{1-3}$hydroxy alkyl, $C_{1-3}$dihydroxyalkyl, $C_{1-3}$alkyl-$CONHR_{12}$ wherein $R_{12}$ is a monoglycosidic group derived from D or L pentoses or hexoses (chosen in the group consisting of ribose, arabinose, glucose, galactose, fructose, glucosamine, galactosamine and their N-acetylated derivatives), $C_{1-3}$alkyltetrazole, $C_{1-3}$alkyl-COOH or wherein $R_9R_{10}$ are joined together to form with the N atom a morpholine or a piperidine ring and where $R_{11}$ is a $C_{1-3}$ alkyl chain, or a $C_{2-4}$ amino-alkyl chain;

$NHCOR_8$ wherein $R_8$ is a cyclohexane containing from 2 to 4 OH groups, a $C_{1-8}$ alkylchain containing a polar group (chosen in the group consisting of $NH_2$, COOH, $CONHR_{12}$ (wherein $R_{12}$ is as hereabove defined) or [1,4']bipiperidine)

COOH, $COOR_{17}$ or $CONHR_{12}$, wherein $R_{12}$ is as hereabove defined and $R_{17}$ is as $R_{12}$ or a group 4-nitrobenzyl and $R_{12}$ is a monoglycosidic group derived from D or L pentoses or hexoses (chosen in the group consisting of ribose, arabinose, glucose, galactose, fructose, glucosamine, galactosamine and their N-acetylated derivatives).

$R_5$, $R_6$, $R_7$ are H.

Likewise preferred are isomers that present an R configuration on the carbon atom that carries the $R_3$ and $R_7$ substituents.

Pharmaceutically acceptable salts of compounds of formula (I) include the salts with inorganic acids (such as, hydrochloric acid, hydrobromic acid, hydrogen iodide, sulphuric acid, nitric acid, phosphoric acid) and organic acids (such as, acetic, propionic, succinic, malonic, citric, tartaric, metasulphonic, para-toluenesulphonic acids), as well as salts of pharmaceutically acceptable bases, both inorganic (such as, hydroxides of sodium, potassium, calcium, magnesium, zinc and aluminium) and organic bases (such as, amines like methyl amine, diethyl amine, triethyl amine, ethyl amine, tromethamine or piperidine).

According to the invention, the compounds of formula (I) containing peptide or pseudopeptide bonds may be obtained by means of classical condensation methods using techniques known in the literature. The general method chosen by us for preparing the peptide compounds ($X_1$–$X_4$=— CONR—, —NRCO—) involves the synthesis in solution of the linear peptide chain using amino acids, dicarboxyl; or diamine derivatives suitably protected and, after selective deprotection of the C- and N-terminals, cyclization in polar organic solvents in diluted solution. As method of activation of the carboxyl groups, that using PyBOP and DIEA in DMF or HBT and EDC in DMF are generally preferred.

To provide an example, FIG. 1 presents the general synthesis of compounds of formula (I) in which $X_1$=$X_2$=$X_3$=$X_4$=—CONH—.

The dicarboxyl precursors 7 containing the $R_4$ group, and the diamine precursors 4 containing the $R_3$ and $R_7$ groups were prepared using methods described in the literature.

In particular, the synthesis of the succinic derivatives, with $R_4$=alkyl or $(CH_2)_n$—Ar, is described by R. Conrow et al., J. Org. Chem., 1986, 51, 938 and by S. G. Cohen et al., J. Am. Chem. Soc., 1968, 90, 3495, whilst in the case of $R_4$=H, amine group, hydroxyl group or carboxyl group, the following were respectively used: succinic anhydride, aspartic acid, malic acid or carboxysuccinic acid appropriately protected.

The synthesis of the ethylene diamine derivatives containing the $R_3$, $R_7$ groups was performed starting from the corresponding N-protected amino acids by reduction of the carboxyl to alcohol with $BH_3.THF$ (C. F. Stanfield et al., J. Org. Chem., 1981, 46, 4797, 4799; I. R. Ollmann et al., Bioorg. Med. Chem., 1995, 3, 969), conversion to azide via the corrisponding mesylate and subsequent reduction to amino group (P. G. Mattingly, Synthesis, 1990, 366; P. M. O'Brien et al., J. Med. Chem., 1994, 37, 1810).

The compounds containing reduced peptide bonds ($X_1$–$X_4$=—$CH_2$—NR—, —NR—$CH_2$—) were synthesized in solution according to known methods, such as reductive amination of the aldehyde of an amino acid with the amine function of a protected amino acid or peptide, in the presence of $NaCNBH_4$ as reducer in DMF/AcOH (K. A. Jacobson et al., J. Med. Chem., 1983, 26, 492; R. F. Borch et al. J. Am. Chem. Soc., 1971, 93, 2897; J. P. Salvi et al., Tetr. Lett., 1994, 35, 1181). The aldehydes were obtained by reduction with $LiAlH_4$ of the corresponding protected amino acids, N,O-dimethylhydmxy-amates according to the method described by J. A. Feherentz et al., Synthesis, 1983, 676 and Int. J. Peptide Res., 1985, 26, 236.

The compounds of formula 10 wherein $R_4$ is $NH_2$ or COOH can be derivatized into compounds of formula I wherein $R_4$ is $NR_9R_{10}$, guanidine, tetrazole, $NHCOR_8$, $CONHR_8$, $COOR_{17}$, $CONHR_{12}$, wherein $R_9$, $R_{10}$, $R_8$, $R_{12}$ and $R_{17}$ are as above defined, according to known methods.

The compounds of formula (I) as specified above have proved to be powerful antagonists of the NK-2 receptor of tachykinins, and hence can be administered as agents capable of controlling any central or peripheral manifestation due to excessive activation of tachykinergic neurons, and in particular excessive contraction of smooth muscle in any pathological condition in which release of tachykinins concurs in the genesis of the corresponding disorders.

In particular, the bronchospastic and inflammatory component of asthma, of coughing, of pulmonary irritation, intestinal spasms, spasms of the biliary tract, and local spasms of the bladder and ureter in the course of cystitis and kidney infections and colics may be considered conditions in which the administration of the compounds of formula (I), as NK-2 antagonists, may prove effective.

The use as anxiolytic agents should also be considered for those compounds that are provided with the appropriate chemico-physical characteristics for penetration into the CNS.

The compounds of formula (I) that are the subject of the present invention are suited for administration for therapeutic purposes to higher animals and man through the parenteral, oral, inhalational and sublingual routes, achieving pharmacological effects according to the properties described above. For administration through parenteral (intravenous, intramuscular, and intradermal) routes, sterile or lyophilized preparations are used. As far as the nasal, inhalational and sublingual instillation routes are concerned, aqueous solutions, aerosol preparations, powders or capsules are used according to the particular case.

The doses of active principle in the aforesaid compositions may range between 0.02 and 10 mg/kg of body weight.

The invention will now be illustrated in the examples that follow, which, however, have no limiting effect.

EXAMPLE 1

Cyclo{-Suc-Trp-Phe-[(R)—NH—CH($CH_2C_6H_5$)— $CH_2$—NH—]}

(compound of formula (I) where: $X_1$=$X_2$=$X_3$=$X_4$=— CO—NH—; $R_1$=—$CH_2$-(indol-3-yl); $R_2$=$R_3$=—$CH_2$— $C_6H_5$; $R_4$=$R_5$=$R_6$=$R_7$=H; m=h=0, f=g=1; the carbon atoms C—$R_1$ and C—$R_2$ have an S configuration, whereas C—$R_3$ has an R configuration)

a) Synthesis of BOC-Trp-Phe-OH Dipeptide

Di-tert-butyl carbonate (3.4 g) was added to a solution of H-Trp-Phe-OH (5 g) in dioxane (30 ml), $H_2O$ (15 ml) and NaOH 1M (15.6 ml), cooled to 0–5° C. under stirring. The reaction mixture was kept stirred for 2 hours, and then concentrated and extracted with pentane (2×20 ml). The aqueous phase was cooled with ice, with the addition of AcOEt (50 ml), $KHSO_4$ to obtain pH 2–3, separated and extracted with AcOEt (2×50 ml). The re-united organic phases were washed with brine (50 ml), vacuum dried and evaporated at 30° C. to obtain 6 g of the desired compound as a white semi-solid residue.

TLC: r.f. 0.55 (chloroform/cyclohexane/ACOH/$H_2O$=45/45/5/5), 0.52. ($CHCl_3$/MeOH=9/1).

b) Synthesis of (R)-1-benzyl-2-benzyloxycarbonylamino-ethyl amine

The synthesis was carried out following the method described by P. G. Mattingly, Synthesis, 1990, 366, starting from BOC-D-phenylalaninol c) Synthesis of BOC-Trp-Phe-[(R)—NH—CH($CH_2$— $C_6H_5$)—$CH_2$—NH-Z] (5)

(R)-1-benzyl-2-benzyloxycarbonylamino ethyl amine (750 mg), PyBOP (1.37 g), and DIEA (0.9 ml) were added to a solution of BOC-Trp-Phe-OH (1.19 g, 2.63 mmol.) in anhydrous DMG (10 ml) under nitrogen.

The reaction mixture was kept stirred overnight at room temperature, AcOEt (80 ml) was added, and the mixture was washed with HCl 1N (3×30 ml), $Na_2CO_3$ 5% (3×30 ml), and $H_2O$ (30 ml). The organic phase was vacuum evaporated at 30° C. to obtain 1.8 g of an ivory-coloured solid residue.

The crude compound was purified by washing in suspension with AcOEt under heat and with MeOH at room temperature to obtain 1.15 g of the desired product 5 as a white solid. MS(TS): [$MH^+$]=718 d) Synthesis of H-Trp-Phe-[(R)—NH—CH($CH_2$—$C_6H_5$)— $CH_2$—NH-Z] (6)

TFA (6 ml) was added, under stirring and at room temperature, to a suspension of the compound 5 (1.1 g) in $CHCl_3$ (30 ml), and a clear solution was seen to form immediately. The reaction mixture was kept stirred for 1.5 hours, and the disappearance of the precursor was monitored by means of HPLC analysis. After evaporation of the solvent, the residue was diluted with AcOEt (100 ml), washed with $NaHCO_3$ 5% (2×30 ml) and brine (30 ml).

The organic phase was dried with $MgSO_4$ and vacuum evaporated at 30° C. The solid residue was purified by means of flash-chromatography ($CHCl_3$/MeOH=95/5) to obtain 821 mg of the desired compound 6 as a white solid.

TLC: r.f. 0.50 ($CHCl_3$/MeOH=9/1).

e) Synthesis of HO-Suc-Trp-Phe-[(R)—NH—CH($CH_2$— $C_6H_5$)—$CH_2$—NH-Z] (Compound 8 where: $PG_2$=OH; $PG_1$=Z)

$NEt_3$ (0.095 ml) and succinic anhydride (68 mg) were added to a solution of compound 6 (420 mg) in anhydrous DMF (10 ml) under stirring and at room temperature. The reaction mixture was kept stirred at room temperature for 4 hours.

After evaporation of the solvent, the residue was suspended in $H_2O$ and kept stirred for 5 minutes. The solid was filtered and washed in suspension twice using MeOH to obtain 242 mg of the desired compound 8 as a white solid.

TLC: r.f. 0.50 ($CHCl_3$/MeOH=8/2).

f) Synthesis of HO-Suc-Trp-Phe-[(R)—NH—CH($CH_2$— $C_6H_5$)—$CH_2$—$NH_2$] (9)

The compound 8 (225 mg) was suspended in MeOH (10 ml) and hydrogenated in the presence of Pd/C 10% (50 mg) at atmospheric pressure and room temperature. HPLC analysis after 4 hours showed that the precursor had disappeared completely.

The catalyst was filtered and washed with MeOH. After evaporation of the solvent, 158 mg of the desired compound 9 were obtained as a white solid.

m.p.=142–4° C.; TLC: r.f. 0.70 (n-butanol/AcOH/H$_2$O= 6/2/2)

g) Synthesis of cyclo{Suc-Trp-Phe-[(R)—NH—CH(CH$_2$—C$_6$H$_5$)—CH$_2$—NH—]}-(10) PyBOP (145 mg) and DIEA (0.09 ml) were added to a solution of compound 9 (148 mg) in anhydrous DMF (5 ml) stirred under nitrogen.

The reaction mixture was kept stirred for 5 hours and, after evaporation of the solvent, the residue was suspended in AcOEt, kept stirred for 10 minutes, and filtered, to obtain 100 mg of a solid product.

Part of the product (50 mg) was purified by HPLC to obtain 18 mg of the desired compound 10 as a white solid. MS (TS): [MH$^+$]=566; 1H-NMR (DMSO): d 2.15–2.35 (m, 2H), 2.55–2.85 (m, 8H), 2.96–3.04 (m, 2H), 3.90–4.02 (m, 1H), 4.03–4.15 (m, 1H), 4.25–4.42 (m, 1H), 6.71 (d, 1H), 6.90–7.42 (m, 16H), 8.09 (m, 1H), 8.50 (d, 1H), 10.82 (s, 1H).

Following the procedure described in Example 1, the compounds specified below were obtained:

EXAMPLE 2

Cyclo{-Suc-Trp-Phe-[(S)—NH—CH(CH$_2$C$_6$H$_5$)—CH$_2$—NH—]}

(compound of formula I in which the substituents are defined as in Example 1, but all the C—R$_1$, C—R$_2$ and C—R$_3$ atoms have an S configuration) 1H-NMR (DMSO): d 1.95–2.32 (m, 2H), 2.34–2.90 (m, 6H), 2.92–3.18 (m, 2H), 3.60–3.82 (m, 1H), 4.00–4.40 (m, 4H), 6.90–7.36 (m, 14H), 7.39–7.54 (m, 2H), 7.64 (d, 1H), 7.88 (t, 1H), 8.27 (d, 1H), 10.78 (s, 1H).

EXAMPLE 3

Cyclo{-Suc-Trp-Phe-[(R)—NH—CH(CH$_2$C$_6$H$_{11}$)—CH$_2$—NH—]}

(compound of formula I in which X$_1$=X$_2$=X$_3$=X$_4$=CO—NH—; R$_1$=CH$_2$-(indol-3-yl); R$_2$=—CH$_2$—C$_6$H$_5$; R$_3$=—CH$_2$—C$_6$H$_{11}$; R$_4$=R$_5$=R$_7$=H; m=h=0, f=g=1; the carbon atoms C—R$_1$ and C—R$_2$ have an S configuration, whereas C—R$_3$ has an R configuration) 1H-NMR (DMSO): d 0.65–0.95 (m 2H), 1.00–1.38 (m, 6H), 1.45–1.75 (m, 5H), 2.05–2.30 (m, 2H), 2.40–2.85 (m, 6H), 3.20–3.60 (m, 1H), 3.61–3.78 (m, 1H), 3.80–3.96 (m, 1H), 3.98–4.10 (m, 1H), 4.38–4.55 (m, 1H), 8.47 (d, 1H), 6.90–7.45 (m, 11H), 8.02 (m, 1H), 8.47 (d, 1H), 10.78 (d, 1H).

EXAMPLE 4

Cyclo{-Suc-Trp-Phe-[(R)—NH—CH(CH$_2$C$_6$H$_4$(4-OCH$_3$))—CH$_2$—NH—]}

(compound of formula I in which X$_1$=X$_2$=X$_3$=X$_4$=CO—NH—; R$_1$=—CH$_2$-(indol-3-yl); R$_2$=—CH$_2$—C$_6$H$_5$; R$_3$=—CH$_2$—C$_6$H$_4$(4-OCH$_3$): R$_4$=R$_5$=R$_6$=R$_7$=H; m=h=0, f=g=1; the carbon atoms C—R$_1$ and C—R$_2$ have an S configuration, whereas C—R$_3$ has an R configuration) 1H-NMR (DMSO): d 2.13–2.37 (m, 2H), 2.50–2.85 (m, 8H), 3.25–3.50 (m, 1H), 3.58–3.80 (m, 4H), 3.85–4.00 (m, 1H), 4.02–4.18 (m, 1H), 4.28–4.45 (m, 1H), 6.65–7.47 (m, 16H), 8–02–8.16 (m, 1H), 8.48 (d, 1H), 10.80 (s, 1H).

EXAMPLE 5

Cyclo{-Suc-Trp(5F)-Phe[(R)—NH—CH(CH$_2$C$_6$H$_5$)—CH$_2$—NH—]}

(compound of formula I, in which R$_1$=—CH$_2$-(5-fluoroindol-3-yl), and the other substituents are as defined in Example 1) MS(ES+): [MH+]=584

EXAMPLE 6

Cyclo{-Suc-Trp(Me)-Phe[(R)—NH—CH(CH$_2$C$_6$H$_5$)—CH$_2$—NH—]}

(compound of formula I, in which R$_1$=CH$_2$-(N-methylindol-3-yl), and the other substituents are as defined in Example 1) MS(ES+):[MH+]=580

EXAMPLE 7

Cyclo{-Suc-Phe(3,4-Cl)-Phe-[(R)—NH—CH(CH$_2$C$_6$H$_5$)—CH$_2$—NH—]}

(compound of formula I, in which R$_1$=-(3,4-dichlarobenzyl), and the other substituents are as defined in Example 1) MS(ES+):[MH+]=595

EXAMPLE 8

Cyclo{-Suc-Trp-Phe(3,4-Cl)-[(R)—NH—CH(CH$_2$C$_6$H$_5$)—CH$_2$—NH—]}

(compound of formula I, in which R$_2$=-(3,4-dichlarobenzyl), and the other substituents are as defined in Example 1) (MS(ES+):[MH+]=634

EXAMPLE 9

Cyclo{-Suc-Trp-Tyr-[(R)—NH—CH(CH$_2$C$_6$H$_5$)—CH$_2$—NH—]}

(compound of formula I, in which R$_2$=-(4-hydroxybenzyl), and the other substituents are as defined in Example 1) (MS(ES+):[MH+]=582

EXAMPLE 10

Cyclo{-Suc-Trp-Phe-[(R)—NH—CH(CH$_2$C$_6$H$_3$-3,4-diCl)-CH$_2$—NH—]}

(compound of formula I, in which R$_3$=-(3,4-dichlorobenzyl), and the other substituents are as defined in Example 1) (MS(ES+):[MH+]=634

EXAMPLE 11

Cyclo{-Suc-Trp-Phe-[(R)—NH—CH(CH$_2$C$_6$H$_4$-4-OH)—CH$_2$—NH—]}

(compound of formula I, in which R$_3$=-(4-hydroxybenzyl), and the other substituents are as defined in Example 1) (MS(ES+):[MH+]=582

EXAMPLE 12

Cyclo{-Suc-Trp-Phe-[(R)—NH—CH(CH$_2$—CH$_2$—C$_6$H$_5$)—CH$_2$—NH—]}

(compound of formula I, in which R$_3$=—CH$_2$—CH$_2$—C$_6$H$_5$, and the other substituents are as defined in Example 1) (MS(ES+):[MH+]=580

EXAMPLE 13

Cyclo{-Suc-Trp-Phe-[(R)—NH—CH(CH$_2$-2-naphthyl)-CH$_2$—NH—]}

(compound of formula I, in which R$_3$=—CH$_2$-(2-naphthyl), and the other substituents are as defined in Example 1) (MS(ES+):[MH+]=616

EXAMPLE 14

Cyclo{-Suc-Trp-Phe-[(R)—NH—CH(CH$_2$-indol-3-yl)-CH$_2$—NH—]}

(compound of formula I, in which R$_3$=—CH$_2$-(indol-3-yl), and the other substituents are as defined in Example 1) (MS(ES+):[MH+]=605

EXAMPLE 15

Cyclo{-Suc-Trp-Phe-[(R)—NH—CH(CH$_2$-5-F-indol-3-yl)—CH$_2$—NH—]}
(compound of formula I, in which R$_3$=—CH$_2$-(5-fluoroindol-3-yl), and the other substituents are as defined in Example 1) (MS(ES+):[MH+]=623

EXAMPLE 16

Cyclo{-Suc-Trp-Phe-[(R)—NH—CH(CH$_2$C$_6$H$_4$-3-F)—CH$_2$—NH—]}
(compound of formula I, in which R$_3$=—CH$_2$C$_6$H$_4$-3-F, and the other substituents are as defined in Example 1) (MS(ES+):[MH+}=584

EXAMPLE 17

Cyclo{-Suc-Trp-Phe-[(R)NH—CH(CH$_2$—C$_6$H$_3$-3,4-diF-CH$_2$—NH]—}
(compound of formula (I) wherein R$_3$=-(3,4-difluorobenzyl) and the other substituents are as defined in Example 1 MS (ES+): [MH+]=602

EXAMPLE 18

Cyclo{-Suc-Trp-Phe-[(R)NH—CH(CH$_2$—C$_6$H$_4$-4-CF$_3$—CH$_2$—NH]—}
(compound of formula (I) wherein R$_3$=-(4-trifluoromethylbenzyl) and the other substituents are as defined in Example 1) MS (ES+): [MH+]=634

EXAMPLE 19

Cyclo{-Suc-Trp-Phe-[(R)—NH—CH$_2$—CH(CH$_2$C$_6$H$_5$)—NH—]}
(compound of formula (I) where: X$_1$=X$_2$=X$_3$=X$_4$=—CO—NH—; R$_1$=—CH$_2$-(indol-3-yl); R$_2$=R$_3$=—CH$_2$—C$_6$H$_5$; R$_4$=R$_5$=R$_6$=R$_7$=H; f=h=0; m=g=1; the carbon atoms C—R$_1$ and C—R$_2$ have an S configuration, whereas C—R$_3$ has an R configuration)

a) Synthesis of (R)-2-tert-butoxycarbonylamino-3-phenyl-propylamine

The synthesis was performed according to the method described by P. G. Mattingly, Synthesis, 1990, 366, starting from BOC-D-phenylalaninol.

b) Synthesis of Z-Trp-Phe-[(R)—NH—CH(CH$_2$—C$_6$H$_5$)—NH-BOC] (5)

(R)-2-tert-butoxycarbonylamino-3-phenyl-propylamine (titre 65%, 1.1 g), PyBOP (1.45 g), and DIEA (0.98 ml) were added to a solution of Z-Trp-Phe-OH (1.4 g) in anhydrous DMF (15 ml) under nitrogen. The reaction mixture was kept stirred overnight at room temperature, AcOEt (100 ml) was added, and the mixture was washed with HCl 1N (3×30 ml), Na$_2$CO$_3$ 5% (3×30 ml), and H$_2$O (30 ml). During the washings, the product partly precipitated, and was filtered and re-united to the organic phase. After vacuum evaporation of the solvent, the residue (2.4 g) was washed in suspension with AcOEt and vacuum dried on P$_2$O$_5$, to obtain 1.79 g of the desired compound 5 as a white solid.

TLC: r.f. 0.86 (CHCl$_3$/MeOH=95/5); r.f. 0.78 (AcOEt).

c) Synthesis of H-Trp-Phe-[(R)—NH—CH$_2$—CH(CH$_2$—C$_6$H$_5$)—NH-BOC] (6)

A suspension of the compound 5 (1.7 g) in MeOH (350 ml) was hydrogenated in the presence of Pd/C 10%, at atmospheric pressure and room temperature, until the precursor disappeared (HPLC analysis). After elimination of the catalyst by filtration and vacuum evaporation of the solvent, the residue was washed in suspension with AcOEt to obtain 890 mg of the desired compound 6 as a white solid.

TLC: r.f. 0.38 (CHCl$_3$/MeOH=9/1), r.f. 0.26 (AcOEt).

d) Synthesis of HO-Suc-Trp-Phe-[(R)—NH—CH$_2$—CH(CH$_2$—C$_6$H$_5$)—NH-BOC] (compound 8 where: PG$_2$=OH; PG$_1$=BOC)

Succinic anhydride (158 mg) and NEt$_3$ (0.21 ml) were added to a solution of compound 6 (840 mg) in anhydrous DMF (20 ml) under nitrogen. The reaction mixture was kept stirred at room temperature overnight. After vacuum evaporation of the solvent at a temperature of 30° C., the residue was treated with H$_2$O at 40–50° C., filtered, washed in suspension with MeOH (15 ml), and vacuum dried to obtain 600 mg of the desired compound 8 as a white solid.

TLC: 0.63 (CHCl$_3$/MeOH=8/2).

e) Synthesis of HO-Suc-Trp-Phe-[(R)—NH—CH$_2$—CH(CH$_2$—C$_6$H$_5$)—NH$_2$.TFA (9 TFA)

TFA (2 ml) was added, under stirring, to a suspension of compound 8 (560 mg) in CH$_2$Cl$_2$ (15 ml), and a clear solution was obtained. After 2 hours at room temperature, the solvent was evaporated, and the residue diluted with ether, filtered and dried to obtain 500 mg of the desired compound 9 TFA as an ivory-coloured solid.

TLC: 0.58 (CHCl$_3$/MeOH=8/2), 0.74 (n-butanol/AcOH/H$_2$O=6/2/2).

f) Synthesis of cyclo{-Suc-Trp-Phe-[(R)—NH—CH$_2$—CH(CH$_2$—C$_6$H$_5$)—NH—]} (10)

PyBOP (447 mg), and DIEA (0.37 ml) were added, under nitrogen, to a solution of 9 TFA (500 mg) in anhydrous DMF (20 ml). The reaction mixture was kept stirred overnight at room temperature, After evaporation of the solvent, the residue was washed in suspension with citric acid 5% and H$_2$O. The product was dried on P$_2$O$_5$, washed in suspension using AcOEt and MeOH under heat, to obtain 110 mg of a solid. A portion was purified by HPLC to obtain 25 mg of the desired compound 10 as a white solid.

1H-NMR (DMSO): d 2.10–2.40 (m, 4H), 2.45–2.58 (m, 1H), 2.60–3.05. (m, 7H), 3.80–3.90 (m, 1H), 3.92–4.05 (m, 1H), 4.20–4.38 (m, 1H), 6.90–7.40 (m, 16H), 7.52–7.58 (m, 1H), 8.11 (d, 1H), 8.37 (d, 1H), 10.79 (s, 1H).

EXAMPLE 20

Cyclo{-Suc-Trp-Phe-[(S)—NH—CH$_2$—CH(CH$_2$C$_6$H$_5$)—NH—]}
(compound of formula I in which the substituents are defined as in Example 19, except for the fact that C—R$_3$ has an S configuration).

The compound was obtained following a procedure similar to that described for

EXAMPLE 19

1H-NMR (DMSO): d 1.98–2.26 (m, 2H), 2.40–2.88 (m, 8H), 2.98–3.11 (m, 1H), 3.66–3.84 (m, 1H), 3.98–4.23 (m, 2H), 4.40–4.58 (m, 1H), 6.89–7.48 (m, 17H), 8.10 (d 1H), 8.44 (d, 1H), 10.83 (s. 1H).

Proceeding in a similar way as that described in Example 1 above, the following compounds were obtained:

EXAMPLE 21

Cyclo{-Trp-Phe-[(R)—NH—CH(CH$_2$—C$_6$H$_5$)—CH$_2$—NH—]—(CH$_2$)$_3$CO—}
(compound of formula I, in which R$_3$=—CH$_2$—C$_6$H$_5$ and X$_3$=—CH$_2$—NH—, and the other substituents are as defined in Example 1. MS (ES+): [MH+)=552.

EXAMPLE 22

Cyclo{-Trp-Phe-[(R)—NH—CH(CH$_2$—C$_6$H$_5$)—CH$_2$—N(CH$_3$)]—(CH$_2$)$_3$CO—}
(compound of formula I, wherein R$_3$=—CH$_2$—C$_6$H$_5$ and X$_3$=—CH$_2$N(CH$_3$)— and the other substituents are as defined in Example 1. MS(ES+):[MH+]=566.

EXAMPLE 23

Cyclo{-Suc[1(S)—NH$_2$]-Trp-Phe-[(R)NH—CH(CH$_2$—C$_6$H$_5$)—CH$_2$NH]—}

(compound of formula I wherein h=1, g=0, R$_4$=—NH$_2$ and the other substituents are as defined in Example 1 while the carbon atom C—R$_4$ has configuration S).

a) Synthesis of Boc-Asp[Trp-Phe-[(R)NH—CH(CH$_2$—C$_6$H$_5$)—CH$_2$—NH-Z]-OBz](compound 8 wherein: PG$_2$=OBzl, PG$_1$=Z To a solution of compound 6 (see Example. 1d) (650 mg) in anhydrous DMF (30 ml) Boc-Asp-OBzl (340 mg), PyBOP (656 mg) and ET$_3$N (0.4 ml) are added under stitrring at room temperature. The mixture is stirred for 2 h at room temperature. After evaporation of the solvent under vacuum the residue was treated with H$_2$O giving a solid residue which is filtered, washed with water and dryed. The solid was recrystallized from ethanole giving 640 mg of the desired compound 8 in the form of a white solid.

MS (ES+): [MH+]=923; HPLC performed in the following conditions: silica column C$_{18}$ particles size 5 μm and pores of 100 A (analitical data: 20% carboon and C$_{18}$ Surface Coverage 3.3 μmoles/m$^2$), lenght: 3.9×150 mm; mobile phase having a linear gradient of acetonitrile containing 0.1%(v/v) TFA (phase B) against aqueous TFA 0.1% (v/v) (phase A), from 20% to 80% in B in 20 minutes at a flux of 3 ml/min; determination by UV at 220 nm. Retentio time: Rt=21.1 min.

b) Synthesis of Boc-Asp[Trp-Phe-[(R)NH—CH(CH$_2$—C$_6$H$_5$)—CH$_2$—NH$_2$]}—OH (9)

The compound 8 (of Example 23a) (600 mg) was solved in DMF (2 ml) and diluted with MeOH (30 ml), hydrogenated in the presence of Pd/C 10% (100 mg) at room pressure and temperature for 5 h. The catalyser was filtered and washed with MeOH. After evaporation of the solvent 420 mg of the desired product 9 were obtained in the form of a white solid.

MS(ES+):[MH+]=663; HPLC (same conditions as above): Rt=11.07.

c) Synthesis of cyclo{-Suc[1(S)NH-BOC]-Trp-Phe[(R)NH—CH(CH$_2$—CH$_6$H$_5$)—CH$_2$—NH]—} (10)

To a solution of compound 9 (see, example 23b) (7.2 g) in anhydrous DMF (900 ml) 4 g of HBT and 2 g of EDC were added under stirring and nitrogen atmosphere. The mixture was stirred for 5 h and, after evaporation of the solvent, the residue was treated with an aqueous solution of KHSO$_4$ 5% and extracted in ethylacetate.

The organic phase was washed with brine, NaHCO$_3$ 5% and again with brine, dried and evaporated the yellow solid obtained (5.2 g) was crystallized from isopropanole/water 1/1 giving 3.2 g of a white solid. MS(ES+):[MH+]=681; HPLC (same conditions as above): Rt=14.8.

d) Synthesis of cyclo{-Suc[(1(S)NH$_2$]-Trp-Phe-[(R)NH—CH(CH$_2$—C$_6$H$_5$)—CH$_2$—NH]} (10)

To a suspension of compound 10 (see example 23d) (1 g) in CH$_2$Cl$_2$ (20 ml) TFA (7 ml) was added under stirring at 0° C. giving a clear solution; thereafter the temerature is raised up to room temperature. The mixture was left at room temperature for 90 minutes and then the solvent was evaporated and the residue was treated with NaHCO$_3$ and water and extracted in ethylacetate. The organic phase was washed with brine, dried and evaporated giving a solid (800 mg).

MS(ES+).[MH+}=581; HPLC (same conditions as above said): Rt=9.4.

A sample of 20 mg is purified by HPLC giving 15 mg of trifluoroacetate: cyclo{-Suc[1(S)NH$_2$]-Trp-Phe-[(R)NH—CH(CH$_2$—C$_6$H$_{5)-CH2}$—NH]—}.TFA (10 TFA) MS(ES+): [MH+]=581; HPLC: Rt=9.4 (same conditions as above);

1H-NMR (DMSO): δ 2.60–2.90 (m, 8H), 3.05–3.11 (m, 1H), 3.63–3.71 (m, 1H), 4.07–4.13 (m, 3H), 4.32–4.38 (m, 1H), 6.90–7.45 (m, 17H), 8.07 (bs, NH$_3^+$), 8.22–8.28 (m, 1H), 8.57 (d, 1H), 10.82 (s, 1H).

Following the procedure described in Example 23 the following compounds were obtained:

EXAMPLE 24

Cyclo{-Suc[1(R)—NH$_2$]-Trp-Phe-[(R)NH—CH(CH$_2$—C$_6$H$_5$)—CH$_2$NH]—}

(compound of formula I wherein h=1, g=0, R$_4$=—NH$_2$ and the other substituents are as defined in Example 1 while the carbon atom C—R$_4$ ha configuration R) MS (ES+): [MH+]=581

EXAMPLE 25

Cyclo{-Suc[2(S)—NH$_2$]-Trp-Phe-[(R)NH—CH(CH$_2$—C$_6$H$_5$)—CH$_2$NH]—}

(compound of formula I wherein h=1, g=0, R$_4$=—NH$_2$ and the other substituents are as defined in Example 1 while the carbon atom C—R$_4$ ha configuration S) MS (ES+): [MH+]=581

EXAMPLE 26

Cyclo{-Suc[2(R)—NH$_2$]-Trp-Phe-[(R)NH—CH(CH$_2$—C$_6$H$_5$)—CH$_2$NH]}

(compound of formula I wherein h=1, g=0, R$_4$=—NH$_2$ and the other substituents are as defined in Example 1 while the carbon atom C—R$_4$ ha configuration R) MS (ES+): [MH+]=581

EXAMPLE 27

Cyclo{-Suc[1(S)—NH(CH$_3$)]-Trp-Phe-[(R)NH—CH(CH$_2$—C$_6$H$_5$)—CH$_2$NH]—}

(compound of formula I wherein h=1, g=0, R$_4$=—NH(CH$_3$) and the other substituents are as defined in Example 1 while the carbon atom C—R$_4$ ha configuration S) MS (ES+): [MH+]=595

EXAMPLE 28

Cyclo{-Suc[1-COO(CH$_2$—C$_6$H$_4$-4-NO$_2$)]-Trp-Phe-[(R)NH—CH(CH$_2$—C$_6$H$_5$)—CH$_2$NH]—}

(compound of formula I wherein h=1, g=0, R$_4$=—COO(CH$_2$—CH$_6$H$_4$-4-NO$_2$) and the other substituents are as defined in example 23) (diasteroisomeric mixture in respect of C—R$_4$ and separation of the two epimers).

a) Synthesis of Boc-Trp-Phe-[(R)—NH—CH(CH$_2$—C$_6$H$_5$)—CH$_2$—NH$_2$]

The Boc-Trp-Phe-[(R)—NH—CH(CH$_2$—C$_6$H$_5$)—CH$_2$—NH-Z] (5 see example 1c) (1.2 g) was dissolved in a mixture of DMF (30 ml) and MeOH (200 ml) and hydrogenized in the presence of Pd/C 10% (200 mg) at room pressure and temperature, for 4 h. The catalyser was filtered and washed with MeOH, the solvent evaporated giving 700 mg of solid residue.

MS(ES+): [MH+] 584; HPLC (conditions of example 23): Rt=11.1.

b) Boc-Trp-Phe-[(R)—NH—CH(CH$_2$—C$_6$H$_5$)—CH$_2$—NH]—COCH[COO(CH$_2$—C$_6$H$_4$-4-NO$_2$)]CH$_2$COO-tBu 424 mg of 2-(4-nitro-benzyloxycarbonyl)-succinic acid 4-tert-butyl ester were dissolved in DMF (20 ml). To the mixture HOBT (490 mg), EDC and Boc-Trp-Phe-[(R)—NH—CH(CH$_2$—C$_6$H$_5$)—CH$_2$—NH$_2$] were added at 0° C.

under stirring; the temperature was raised to room temperature while stirring for 2 h. The solvent was evaporated and the residue treated with KHSO$_4$ 5% giving a yellow solid which was filtered, washed with NaHCO$_3$ 5%, water and dried.

1.05 g of compound were obtained, MS(ES+):[MH+]=919; HPLC (conditions of Example 23): Rt=20.36
c)H-Trp-Phe-[(R)—NH—CH(CH$_2$—C$_6$H$_5$)—CH$_2$—NH]—COCH[COO(CH$_2$—C$_6$H$_4$-4-NO$_2$)]CH$_2$COOH Boc-Trp-Phe-[(R)—NH—CH(CH$_2$—C$_6$H$_5$)—CH$_2$—NH]—COCH[COO(CH$_2$—C$_6$H$_4$-4-NO$_2$)]CH$_2$COO-tBu (1.05 g) was added in small portions in anhydrous trifluoroacetic acid (20 ml) at 0° C. and the mixture was kept under stirring for 30 minutes, dried and the residue treated with ethyleter; the formed solid was filtered, washed with ethyleter and dried, 850 mg of product were obtained.

MS(ES+):[MH+]=763: HPLC (conditions of example 23): Rt=10.6.
d) Synthesis of cyclo{-Suc[1-COO(CH$_2$C$_6$H$_4$-4-NO$_2$)]-Trp-Phe-[(R)—NH—CH(CH$_2$—C$_6$H$_5$)—CH$_2$—NH—]}

The H-Trp-Phe-[(R)—NH—CH(CH$_2$—C$_6$H$_5$)—CH$_2$—NH]—COCH[COO(CH$_2$C$_6$H$_4$-4-NO$_2$)]CH$_2$COOH (100 mg) was dissolved in DMF (5 ml) and to the mixture PyBOP (80 mg) and Et$_3$N (54 µl) were added stirring for 3 h.

The reaction mixture was dried and the residue dissolved in ethylacetate, the organic phase was washed with KHSO$_4$ 5%, brine, NaHCO$_3$ 5% and brine, dried and concentrated. 90 mg of epimeric mixture was obtained, the epimers were separated by HPLC giving:

30 mg of liophylized solid which in HPLC (conditions of example 23) shows an Rt=15.2. MS(ES+):[MH+]=745.

1H-NMR (DMSO): δ 2.54–2.81 (m, 7H), 3.08–3.17 (m, 1H), 3.34–3.39 (m, 1H), 3.77–3.84 (m, 1H), 4.00–4.10 (m, 3H), 4.37–4.43 (m, 1H), 5.31 (s, 2H), 6.60 (d, 1H9, 6.93–7.42 (m, 16H), 7.62 (d, 2H), 8.24 (d, 2H), 8.60 (d, 1H), 8.66–8.72 (m, 1H), 10.81 (s, 1H) and 7 mg of liophylized solid which in HPLC (conditions of example 23) shows an Rt=15.7. MS(ES+): [MH+]=745.

EXAMPLE 29

Cyclo{-Suc(1-COOH)-Trp-Phe-[(R)—NH—CH(CH$_2$—C$_6$H$_5$)—CH$_2$—NH_]} (compound of formula I, wherein h=1, g=0, R$_4$=—COOH and the other substituents are as defined in Example 1) [epimer which in HPLC (conditions of Example 23) shows an Rt=10.7]

The cyclo{-Suc(1-COO(CH$_2$—C$_6$H$_4$-4-NO$_2$)]-Trp-Phe-[(R)—NH—CH(CH$_2$—C$_6$H$_5$)—CH$_2$—NH_]} which in HPLC (same conditions as in example 23) shows an Rt=15.2 (50 mg) was suspended in a mixture water/isopropanole:1/1 (6 ml) containing K$_2$CO$_3$ (19 mg) and was kept under stirring for 24 h. The solvent was evaporated and the residue was diluted with water and the solution washed with ethylacetate, by adding HCl 1N separated a solid which was extracetd with ethylacetate; the organic phase was washed with brine and dried. By evaporating the solvent mg 35 of a solid residue were obtained.

MS(ES+):[MH+]=610. HPLC (conditions of Example 23): Rt=10.7.

EXAMPLE 30

Cyclo{-Suc(1-COOH)-Trp-Phe-[(R)—NH—CH(CH$_2$—C$_6$H$_5$)—CH$_2$—NH_]} (compound of formula I, wherein h=1, g=0, R$_4$=—COOH and the other substituents ar as defined in Example 1) [epimer which in HPLC (conditions as in Example 23) shows an Rt=11.1]

The cyclo{-Suc(1-COO(CH$_2$—C$_6$H$_4$-4-NO$_2$)]-Trp-Phe-[(R)—NH—CH(CH$_2$—C$_6$H$_5$)—CH$_2$-NH_]} having Rt=15.7 was hydrolized as described in Example 29.

MS(ES+):[MH+]=610; HPLC (same conditions of Example 23): Rt=11.1.

As described in Example 28 the following compounds weer obtained:

EXAMPLE 31

Cyclo}-Suc(1-OH)-Trp-Phe-[(R)—NH—CH(CH$_2$—C$_6$H$_5$)—CH$_2$—NH—]}
(compound of formula I, in which h=1; g=0; R$_4$=—OH, and the other substituents are as defined in Example 1), MS(ES+):[MH+]=582.

EXAMPLE 32

Cyclo{-Suc(2-COOH)-Trp-Phe-[(R)—NH—CH(CH$_2$—C$_6$H$_5$)—CH$_2$—NH—]}
(compound of formula I, in which R$_4$=—COOH, and the other substituents are as defined in Example 1) MS(ES+): [MH+]: 610.

EXAMPLE 33

Cyclo{-Suc(2OH)-Trp-Phe-[(R)—NH—CH(CH$_2$—C$_6$H$_5$)—CH$_2$—NH—]} (compound of formula I wherein: h=0, g=1, R$_4$=OH and the other substituents are as defined in example 1) MS(ES+): [MH+]=582.

The compounds of Examples 23, 24, 25, 26, 27, 29, 30 and 32 can be derivatized as described hereinafter.

EXAMPLE 34

Cyclo{-Suc[1(S)-(2H-tetrazolyl-5-ylmethyl)amino]-Trp-Phe-[(R)—NH—CH(CH$_2$—C$_6$H$_5$)—CH$_2$—NH]—}.TFA (compound of formula I wherein h=1, g=0, R$_4$=-(2H-tetrazolyl-5-ylmethyl)amino and the other substituents are as defined in example 1 while the carbon atom C—R$_4$ has configuration S)
a) Synthesis of, 5-iodomethyl-1-trityl-1H-tetrazole To a suspension of 5-chloromethyl-1H-tetrazole (6.0 g) in chloroform (100 ml) trityl-chloride (14.2 g) was added at 0° C. under nitrogen, and the mixture was stirred up to total solubilization, thereafter a solution of Et$_3$N (7.0 ml) in chloroform (50 ml) was added at 5° C. and the temperature was left raising up to room temperature, the mixture was kept resting for 24 h.

The mixture was treated with ethylacetate (200 ml) and left resting for 6 h, the separated solid was filtered away and to the solution acetone (70 ml) was added, the precipitated solid was collected by filtration and dried giving 9.5 g of 5-chloromethyl-1-trityl-1H-tetrazole which was solubilized in acetone (200 ml) at 60° C. Sodium iodide (5.6 g) was added to the solution which was refluxed for 6 h, by cooling precipitated a compound which was filtered, washed with water and dried giving 5.2 g of a white solid.

TLC: R.f. 0.55 (AcOEt/Cyclohexane: 1/3).
b) Synthesis of cyclo{-Suc[1(S)-(2-trityl-tetrazolyl-5-ylmethyl)amino]-Trp-Phe-[(R)NH—CH(CH$_2$—C$_6$H$_5$)—CH$_2$NH]—}

To 205 mg of cyclo{-Suc[1(S)—NH$_2$]-Trp-Phe-[(R) NH—CH(CH$_2$—C$_6$H$_5$)—CH$_2$NH]—}(compound of example 23) in anhydrous DMF (5 ml) were added, under stirring 5-iodomethyl-1-trityl-1H-tetrazole (147 mg) and thereafter DIEA (0.06 ml) keeping the temperature at 0° C. for 4 h and at room temperature for 3 h. The mixture was treated with water and extracted with ethylacetate, the organic phase was washed with brine and dried. By evaporating the solvent a solid was obtained which was purified by column-chromatography eluting with AcOEt/MeOH=9515. 210 mg of product were obtained. MS(ES+):[MH+]=905; HPLC (conditions of example 23): Rt=15.4.

c) synthesis of cyclo{-Suc[1(S(2-Hl-tetrazolyl-5-ylmethyl)amino]-Trp-Phe-[(R)NH—CH(CH$_2$—C$_6$H$_5$)—CH$_2$NH]—}.TFA To a solution of cyclo{-Suc[1(S)-(2-trityl-tetrazolyl-5-ylmethyl)amino]Trp-Phe-[(R)NH—CH(CH$_2$—C$_6$H$_5$)—CH$_2$NH]-} (90 mg) in anhydrous DMF (5 ml) a solution of HCl 4M in dioxane (0.6 ml) was added at 0°–5° C., the temperature was brought to room temperature and the mixture was left resting up to end of the reaction (14 h at room temperature and 56 h at 5° C.) checking the reaction by HPLC. The solvent was evaporated and the residue treated with AcOEt, the organic phase was washed with brine and dried; evaporating the solvent 30 g of a crude solid are obtained, the solid is purified by HPLC giving 10 g of liophylized solid product.

MS(ES+):[MH+]=663; HPLC (conditions of example 23): Rt=9.0.

1H-NMR (DMSO): δ 2.62–2.92 (m, 8H), 3.16–3.23 (m, 1H), 3.68–3.74 (m, 1H), 4.00–4.14 (m, 3H), 4.25–4.75 (m, 3H), 6.88–7.42 (m, 17H), 8.30–8.37 (m, 1H). 8.54 (d, 1H), 10.82 (s, 1H).

EXAMPLE 35

Cyclo{-Suc[1(S)-(morpholin-4-yl)]-Trp-Phe-[(R)—NH—CH(CH$_2$—C$_6$H$_5$)—CH$_2$—NH]—}.TFA (compound of formula I wherein h=1, g=0, R$_4$=-(morpholin-4-yl) and the other substituents are as defined in example 1 while the carbon atom C—R$_4$ has configuration S)

To a solution of 2.2'-oxydiacetaldheyde (1 mmole), excess, in methanole (20 ml) 58 mg of cyclo{-Suc[1(S)—NH$_2$]-Trp-Phe-[(R)NH—CH(CH$_2$—C$_6$H$_5$)—CH$_2$NH]—} (compound of example 23), 0.2 ml of acetic acid and 12 mg of NaCNBH$_3$ were added. After 2 h the mixture was diluted with water (10 ml), treated with HCl 1N up to pH 3 and the methanole was evaporated; the solution was treated with NaHCO$_3$ 5% and the formed solid was extracted with ethylacetate. The organic phase, after washing with brine and anhydrification, was evaporated giving 58 mg of a solid which was purified by HPLC giving 10 mg of liophylized solid trifluoroacetate.

MS(ES+):[MH+]=651; TLC: R.f.0.20 (CHCl$_3$/MeOH:9/1).

1H-NMR (DMSO): δ 2.62–3.00 (m, 8H), 3.27–3.87 (m, 10H), 4.07–4.15 (m, 3H), 4.32–4.38 (m, 1H), 6.62 (d, 1H), 6.94–7.41 (m, 16H), 8.49–8.64(m, 2H), 10.84 (s, 1H).

Via a similar reductive amination reaction, as described in example 35, the following compounds were obtained:

EXAMPLE 36

Cyclo{-Suc[1(S)—N(CH$_3$)$_2$]-Trp-Phe-[(R)—NH—CH(CH$_2$—C$_{6H5}$)—CH$_2$NH]—}.TFA (compound of formula I wherein h=1, g=0, R$_4$=—N(CH$_3$)$_2$ and the other substituents are as defined in example 1 while the carbon atom C—R$_4$ has configuration S)

The synthesis was performed starting from the compound of example 23 using paraformaldheyde. MS(ES+):[MH+]=609.

EXAMPLE 37

Cyclo{-Suc[1(S)-(piperidin-4-yl)]-Trp-Phe-[(R)—NH—CH(CH$_2$—C$_6$H$_5$)—CH$_2$NH]—}.TFA (compound of formula I wherein h=1, g=0, R$_4$=-(piperidin-4-yl) and the other substituents are as defined in example 1 while the carbon atom C—R$_4$ has configuration S)

The synthesis was performed starting from the compound of example 23 using glutaraldheyde. MS(ES+):[MH+]=649.

EXAMPLE 38

Cyclo{-Suc[1(S)—(N(CH$_2$CH$_2$OH)$_2$)]-Trp-Phe-[(R)—NH—CH(CH$_2$—C$_{6H5}$)—CH$_2$—NH]—}.TFA (compound of formula I wherein h=1, g=0, R$_4$=—N(CH$_2$CH$_2$OH)$_2$ and the other substituents are as defined in example 1 while the carbon atom C—R$_4$ has configuration S)

The synthesis was performed starting from the compound of example 23 using HE glycolaldheyde. MS(ES+):[MH+]=669.

EXAMPLE 39

Cyclo{-Suc[1(S)—(NHCH$_2$CH(OH)CH$_2$OH]-Trp-Phe-[(R)—NH—CH(CH$_2$—C$_6$H$_5$)—CH$_2$—NH]—}.TFA (compound of formula I wherein h=1, g=0, R$_4$=—NHCH$_2$CH(OH)CH$_2$OH and the other substituents are as defined in example 1 while the carbon atom C—R$_4$ has configuration S)

The synthesis was performed starting from the compound of example 24 using D-glyceraldheyde. MS(ES+):[MH+]=655.

EXAMPLE 40

Cyclo{-Suc[1(S)-(3-carboxypropanoyl)amino]-Trp-Phe-[(R)—NH—CH(CH$_2$—C$_6$H$_5$)—CH$_2$—NH]—}. (compound of formula I wherein h=1, g=0, R$_4$=-(3-carboxypropanoyl)amino and the other substituents are as defined in example 1 while the carbon atom C—R$_4$ has configuration S)

To a solution of the compound of Example 23 (100 mg) in anhydrous DMF (2 ml) succinic anhydryde (30 mg) and dimethylamino-piridine (10 mg) were added and the solution was stirred for 16 h; the solvent was evaporated giving a solid which was solubilized in ethylacetate, washed with citric acid 10%, brine and dried. By evaporating the solvent a solid compound was collected (90 mg), which purified by HPLC gave 60 mg of a liophylized solid.

MS(ES+):[MH+]=681; HPLC (conditions as in example 23): Rt=10.8.

1H-NMR (DMSO): δ 2.35–2.82 (m, 12H), 3.25–3.28 (m, 1H), 3.66–3.73 (m, 1H), 3.98–4.12 (m, 2H), 4.33–4.38 (m, 1H), 4.67–4.73 (m, 1H), 6.80 (d, 1H), 6.96–7.39 (m, 16H), 8.16–8.23 (m, 2H), 8.51 (d, 1H), 10.89 (s, 1H).

EXAMPLE 41

Cyclo{-Suc[1(S)-[3-N'-(β-D-glucopiranos-1-yl)-carboxamidopropanoyl]amino]-Trp-Phe-[(R)—NH—CH(CH$_2$—C$_6$H$_5$)—CH$_2$—NH]—} (compound of formula I wherein h=1, g=0, R$_4$=-[3-N'-(β-D-glucopiranos-1-yl)carboxyamidopropanoyll]amine] and the other substituents are as defined in example 1 white the carbon atom C—R$_4$ has configuration S)

The compound of example 40 (90 mg) was dissolved in anhydrous DMF (10 ml) under stirring and in nitrogen atmosphere, to the mixture 55 mg HBT, 25 mg EDC and 24 mg β-D-glucopiranosylamine were added.

The mixture was left stirring overnight and after evaporation of the solvent the resulting oil was treated with citric acid 10% giving a solid which was filtered, washed with water and dried. The 80 mg obtained were purified by HPLC giving 40 mg of a liophylized solid.

MS(ES+):[MH+]=842; HPLC (conditions of example 23): Rt=8.2.

1H-NMR (DMSO): δ 2.31–2.81 (m, 12H), 3.00–3.10 (m, 2H), 3.13–3.65 (m, 5H), 3.66–3.75 (m, 1H), 3.97–4.12 (m, 2H), 4.29–4.36 (m, 1H), 4.65–4.75 (m, 2H), 6.78 (d, 1H), 6.95–7.40 (m, 16H), 8.19–8.27 (m, 2H), 8.35 (d, 1H), 8.51 (d, 1H), 10.82 (s, 1H).

EXAMPLE 42

Cyclo{-Suc[1(S)-[(carboxymethyl)amino]-Trp-Phe-[(R)—NH—CH(CH$_2$—C$_6$H$_5$)—CH$_2$—NH]—} TFA (compound of formula I wherein h=1, g=0, R$_4$=-(carboxymethyl)amino and the other substituents are as defined in example 1 while the carbon atom C—R$_4$ has configuration S)

a) Synthesis of cyclo{-Suc[1(S)-[(ter-butoxycarbonylmethyl)-amino]-Trp-Phe-[(R)—NH—CH(CH$_2$—C$_6$H$_5$)—CH$_2$—NH]—}

To a solution of the compound of example 23 (130 mg) in anhydrous DMF (3 ml) DIEA (0.04 ml) and ter-butyle (0.04 ml) bromoacetate were added, the solution was stirred for 2 h and therefater the mixture was poured in KHSO$_4$ 5%. The formed solid was filtered, washed with NaHCO$_3$, water and dried. 100 mg of product were obtained.

HPLC (conditions of Example 23): Rt=11.3.

b) Synthesis of cyclo{-Suc[1(S)-[(carboxymethyl)amino]-Trp-Phe-[(R)—NH—CH(CH$_2$—C$_6$H$_5$)—CH$_2$—NH]—}.TFA The above collected solid (90 mg) was suspended in CH$_2$Cl$_2$ (5 ml) and TFA (5 ml) was added under stirring at 0° C., the mixture was stirred for 1 h at room temperature. The solution was concentrated and the obtained residue was purified by HPLC giving 40 mg of a liophylized solid.

MS(ES+):MH+]=639; HPLC (conditions of Example 23): Rt=9.4.

EXAMPLE 43

Cyclo{-Suc[1(S)-[N'-(β-D-glucopiranos-1-yl)-carboxyamidomethyl]amino]-Trp-Phe-[(R)—NH—CH(CH$_2$—C$_6$H$_5$)—CH$_2$—NH]—} TFA (compound of formula I wherein h=1, g=0, R$_4$=—[N'-(β-D-glucopiranos-1-yl)carboxyamidomethyl]amine] and the other substituents are as defined in example 1 while the carbon atom C—R$_4$ has configuration S)

The product was obtained starting from the product of Example 42 and β-D-glucopiranosylamine according to the procedure of Example 41.

MS(ES+):[MH+]=800; HPLC (conditions of example 23): Rt=7.6.

EXAMPLE 44 cyclo{-Suc[1(S)-(chinyl)amine]-Trp-Phe-[(R)—NH—CH(CH$_2$—C$_6$H$_5$)—CH$_2$—NH]—} (compound of formula I wherein h=1, g=0, R$_4$=-(chinyl)amine and the other substituents are as defined in example 1 while the carbon atom C—R$_4$ has configuration S)

Chinic acid (50 mg) was solubilized in anhydrous DMF (10 ml) under stirring and nitrogen atmosphere, HBT (220 mg), EDC (100 mg) and the compound obtained in Example 24 (150 mg) were added. The mixture was left under stirring overnight, thereafter the solvent was evaporated and the residue treated with an aqueous solution of KHSO$_4$ 5% and extracted with etrhylacetate.

The organic phase was washed with brine, NaHCO$_3$ 5% and again brine, dried and evaporated; the obtained solid (122 mg) was purified on flash chromatography (SiO$_2$) eluting with chloroform/methanole:8/2; 80 mg of the desired compound were obtained.

MS(ES+):[MH+]=755; HPLC (conditions as in example 23) Rt=10.05.

EXAMPLE 45

Cyclo{-Suc[1(S)-(4-aminobutanoyl)amino]-Trp-Phe-[(R)—NH—CH(CH$_2$—C$_6$H$_5$)—CH$_2$—NH]—} TFA (compound of formula I wherein h=1, g=0, R$_4$=-(4-aminobutanoyl)amino and the other substituents are as defined in example 1 while the carbon atom C—R$_4$ has configuration S)

The product was obtained starting from the product of Example 23 and 4-BOC-aminobutirryc acid according to the procedure of Example 44 followed by elimination of the protecting group BOC.

MS(ES+):[MH+]=666.

EXAMPLE 46

Cyclo{-Suc[1(S)-[(1,4')bipiperidin-1-yl]acetamido]-Trp-Phe-[(R)—NH—CH(CH$_2$—C$_6$H$_5$)—CH$_2$—NH]—} TFA (compound of formula I wherein h=1, g=0, R$_4$=-[(1,4')bipiperidin-1-yl]acetamido and the other substituents are as defined in example 1 while the carbon atom C—R$_4$ has configuration S)

The product was obtained starting from the product of Example 23 and [(1,4')bipiperidin-1-yl]acetic acid according to the procedure of Example 44.

MS(ES+):[MH+]=789.

EXAMPLE 47

Cyclo{-Suc[1-N-(β-D-glucopiranos-1-yl)-carboxyamido]-Trp-Phe-[(R)—NH—CH(CH$_2$—C$_6$H$_5$)—CH$_2$—NH]—} (compound of formula I wherein h=1, g=0, R$_4$=N-(β-D-glucopiranos-1-yl)carboxyamide and the other substituents are as defined in example 1 while the carbon atom C—R$_4$ has configuration S)

The product was obtained starting from the product of Example 29 and β-D-glucopiranosylamine according to the procedure of Example 44.

MS(ES+):[MH+]=771.

EXAMPLE 48

Cyclo{-Suc[1(S)-[N'-(2-N-acetyl-β-D-glucopiranos-1-yl)-carboxyamido]-Trp-Phe-[(R)—NH—CH(CH$_2$—C$_6$H$_5$)—CH$_2$—NH]—} (compound of formula I wherein h=1, g=0, R$_4$=—N'-(2-N-acetyl-β-D-glucopiranos-1-yl)carboxyamide and the other substituents are as defined in example 1 while the carbon atom C—R$_4$ has configuration S)

The product was obtained starting from the acid of Example 29 and 2-N-acetyl-β-D-glucopiranosylamine according to the procedure of Example 44.

MS(ES+):[MH+]=812.

Biological Activity

The compounds described in the present invention act as antagonists of the NK-2 receptor of tachykinins. The biological activity was evaluated in two in-vitro functional tests, using rabbit pulmonary artery (RPA) and hamster trachea (HT), according to the methods described by C. A. Maggi et al., Br. J. Pharmacol., 1990., 100, 588 and P. D'Orléans-Juste et al., Eur. J. Pharmacol., 1986, 125, 37. The activity of the compounds as human NK-2 receptor antagonists was assessed in a binding test using membranes of Chinese hamster ovary (CHO) cells, transfected with the NK-2 receptor of human ileum and the radioligand [$^{125}$I] NKA (Amersham, specific activity 2000 Ci/mmol) at a concentration of 100 pM in competition studies. The substances under examination were tested in a concentration range of from 0.01 nM to 10 mM. At the end of incubation (30 minutes at 20° C.), the samples were filtered on Whatman GF/B filters and employing the Brandel automatic filtration system. Radio-activity was determined by means of a gamma counter (Cobra, Canberra Packard).

The data gathered from the functional studies were expressed as pA$_2$ (O. Arunlakshana and H. O. Schild, Br. J. Pharmacol. Chemother., 1959, 14, 48), and those of the binding studies as pKi (-log Ki calculated using the LIGAND programme: P. J. Munson et al., Anal. Biochem., 1980, 107, 220).

The compounds of the invention proved active in the tests referred to above, with pA$_2$ values of between 5 and 9, the more powerful compounds revealing a higher affinity for the human receptor, with pKi of between 8 and 10.

List of Abbreviations Used

For the nomenclature and abbreviations of amino acids, reference is made to the recommendations of the IUPAC-IUB Joint Commission on Biochemical Nomenclaturs (Eur. J. Biochem., 1984, 138, 9); the amino acids are understood in the S configuration, if not otherwise specified.

The other abbreviations used are the following:

BOC=tert-butoxycarbonyl; Z=benzyloxycarbonyl; -Suc-=succinyl; Bzl=benzyl; PyBOP=(benzotriazol-1-yloxy)tris(pyrrolidine)phosphonium hexafluorophosphate, DIEA=N,N-diisopropylethylamine; NEt$_3$=triethylamine; DMF=N,N-dimethylformamide; NKA=neurochinine A; TFA=trifluoro-acetic acid; HBT=1-hydroxybenzotriazole; EDC=N-(3-dimethylaminopropyl)-N'-ethylcarbodiimide hydrochloride.

The numeration of the substituents on the succinic-group is as follows:

-Suc(1-NH$_2$)—=—CO—CH(NH$_2$)—CH$_2$—CO—
-Suc(2-NH$_2$)—=—CO—CH$_2$—CH(NH$_2$)—CO—.

What is claimed is:

1. A monocyclic compound having the formula (1):

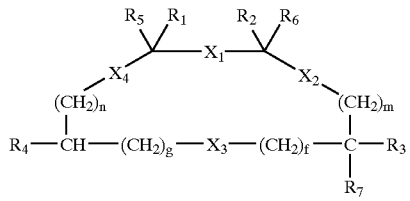

in which:

X$_1$, X$_2$, X$_3$, X$_4$, which may be the same or different from one another, is selected from the group consisting of —CONR—, —NRCO—, —OCO—, —COO—, —CH$_2$NR— and —NR—CH$_2$—, where R is H or a C$_{1-3}$ alkyl or benzyl;

f, g, h, m, which may be the same or different from one another, may be 0 or 1;

R$_1$ and R$_2$ which may be the same or different from one another, represent the side chain of a natural amino acid selected from the group consisting of tryptophan, phenylalanine, tyrosine and histidine, or the side chain of a non-natural amino acid selected from the group consisting of;

tryptophan and phenylalanine, either mono- or di-substituted with residues selected from the group consisting of C$_{1-3}$ alkyl or halo-alkyl, C$_{1-3}$ alkoxyl or amino-alkoxyl, halogen, OH, NH$_2$ and NR$_{13}$R$_{14}$, where R$_{13}$ and R$_{14}$, which may be the same or different from one another, represent a hydrogen or C$_{1-3}$ alkyl group;

R$_3$ is selected from the group consisting of:
linear or branched alkyl having the formula C$_n$H$_{2n+1}$ with n=1–5 (selected from the group consisting of methyl, ethyl, propyl, isopropyl, n-butyl and t-butyl) cycloalkyl or alkylcycloalkyl of formula C$_n$H$_{2n-1}$ with n=5–9 (selected from the group consisting of: cyclopentyl, cyclohexyl and methylcyclohexyl)
(CH$_3$)$_r$—Ar$_1$, where r=1 or 2 and where Ar$_1$ is an aromatic group selected from the group consisting of: α-naphthyl, β-naphthyl, phenyl, indole, said Ar$_1$ group being possibly substituted with a maximum of two residues selected from the group consisting of: C$_{1-3}$ alkyl, CF$_3$, C$_{1-3}$ alkoxyl, Cl, F, OH and NH$_2$;

R$_4$ represents an L-Q group where:
L is a chemical bond or CH$_2$, and
Q is selected from the group consisting of:
OH, NH$_2$, NR$_9$R$_{10}$, OR$_{11}$, and where R$_9$ and R$_{10}$, which may be the same or different from one another, represent a hydrogen or C$_{1-3}$alkyl group, C$_{1-3}$hydroxy alkyl, C$_{1-3}$dihydroxyaklyl, C$_{1-3}$alkyl-CONHR$_{12}$ (wherein R$_{12}$ is a monoglycosidic group derived from D or L pentoses or hexoses (selected from the group consisting of ribose, arabinose, glucose, galactose, fructose, glucosamine, galactosamine N-acetylglucosamine and N-acetylgalactosamine)), C$_{1-3}$alkyltetrazole, C$_{1-3}$alkyl-COOH or wherein R$_9$R$_{10}$ are joined together to form with the N atom a morpholine or a piperidine ring and where R$_{11}$ is a C$_{1-3}$ alkyl chain, or a C$_{2-4}$ amino-alkyl chain;

NHCOR$_8$ wherein R$_8$ is a cyclohexane containing from 2 to 4 OH groups, C$_{1-6}$ alkyl chain containing a polar group (chosen in the group consisting of NH$_2$, COOH, CONHR$_{12}$, (wherein R$_{12}$ is as hereabove defined) or [1,4']bipiperidine))

COOH, COOR$_{17}$ or CONHR$_{12}$, wherein R$_{12}$ is as hereabove defined and R$_{17}$ is as R$_{17}$ or a group 4-nitrobenzyl R$_5$, R$_6$, R$_7$ are H in which the carbon atom that carries the subtituents R$_3$ and R$_7$ has configuration R;

wherein when R$_1$=R$_2$=a side chain of tryptophan and R$_4$=CH$_2$OH then R$_3$ is not isopropyl.

2. A compound according to claim 1 selected from:
(a) Cyclo{-Suc-Trp-Phe-[(R)—NH—CH(CH$_2$C$_6$H$_5$)—CH$_2$—NH]}
(b) Cyclo{-Suc-Trp-Phe-[(S)—NH—CH(CH$_2$C$_6$H$_5$)—CH$_2$—NH]}
(c) Cyclo{-Suc-Trp-Phe-[(R)—NH—CH(CH$_2$C$_6$H$_{11}$)—CH$_2$—NH]}
(d) Cyclo{-Suc-Trp-Phe-[(R)—NH—CH(CH$_2$C$_6$H$_4$(4-OCH$_3$))—CH$_2$—NH]}
(e) Cyclo{-Suc-Trp(5F)-Phe-[(R)—NH—CH(CH$_2$C$_6$H$_5$)—CH$_2$—NH]}
(f) Cyclo{-Suc-Trp(Me)-Phe-[(R)—NH—CH(CH$_2$C$_6$H$_5$)—CH$_2$—NH]}
(g) Cyclo{-Suc-Phe(3,4-Cl)-Phe-[(R)—NH—CH(CH$_2$C$_6$H$_5$)—CH$_2$—NH—]}
(h) Cyclo{-Suc-Trp-Phe(3,4-Cl)—(R)—NH—CH(CH$_2$C$_6$H$_5$)—CH$_2$—NH]}
(i) Cyclo{-Suc-Trp-Tyr-[(R)—NH—CH(CH$_2$C$_6$H$_5$)—CH$_2$—NH]}
(j) Cyclo{-Suc-Trp-Phe-[(R)—NH—CH(CH$_2$C$_6$H$_3$-3,4-diCl)—CH$_2$—NH]}
(k) Cyclo{-Suc-Trp-Phe-[(R)—NH—CH(CH$_2$C$_6$H$_4$-4-OH)—CH$_2$—NH]}
(l) Cyclo{-Suc-Trp-Phe-[(R)—NH—CH(CH$_2$—CH$_2$—C$_6$H$_5$)—CH$_2$—NH]}
(m) Cyclo{-Suc-Trp-Phe-[(R)—NH—CH(CH$_2$-2-napthyl)-CH$_2$—NH]}
(n) Cyclo{-Suc-Trp-Phe-[(R)—NH—CH(CH$_2$-indol-3-yl)-CH$_2$—NH]}
(o) Cyclo{-Suc-Trp-Phe-[(R)—NH—CH(CH$_2$-5-F-indol-3-yl)-CH$_2$—NH]}
(p) Cyclo{-Suc-Trp-Phe-[(R)—NH—CH(CH$_2$—C$_6$H$_4$-3-F)—CH$_2$—NH]}

(q) Cyclo{-Suc-Trp-Phe-[(R)—NH—CH(CH$_2$—C$_6$H$_3$-3,4-diF-CH$_2$—NH]}

(r) Cyclo{-Suc-Trp-Phe-[(R)—NH—CH(CH$_2$—C$_6$H$_4$-4-CF$_3$—CH$_2$—NH]}

(s) Cyclo{-Suc-Trp-Phe-[(R)—NH—CH$_2$—CH(CH$_2$C$_6$H$_5$)—NH]}

(t) Cyclo{-Suc-Trp-Phe-[(S)—NH—CH$_2$—CH(CH$_2$C$_6$H$_5$)—NH]}

(u) Cyclo{-Trp-Phe-[(R)—NH—CH(CH$_2$—C$_6$H$_5$)—CH$_2$—NH]—(CH$_2$)$_3$CO—}

(v) Cyclo{-Trp-Phe-[(R)—NH—CH(CH$_2$—C$_6$H$_5$)—CH$_2$—N(CH$_3$)]—(CH$_2$)$_3$CO—}

(w) Cyclo{-Suc[1(S)—NH$_2$]-Trp-Phe-[(R)NH—CH(CH$_2$—C$_6$H$_5$)—CH$_2$NH]—}

(x) Cyclo{-Suc[1(R)—NH$_2$]-Trp-Phe-[(R)NH—CH(CH$_2$—C$_6$H$_5$)—CH$_2$NH]—}

(y) Cyclo{-Suc[2(S)—NH$_2$]-Trp-Phe-[(R)NH—CH(CH$_2$—C$_6$H$_5$)—CH$_2$NH]—}

(z) Cyclo{-Suc[2(R)—NH$_2$]-Trp-Phe-[(R)NH—CH(CH$_2$—C$_6$H$_5$)—CH$_2$NH]—}

(aa) Cyclo{-Suc[1(S)—NH(CH$_3$)]-Trp-Phe-[(R)NH—CH(CH$_2$—C$_6$H$_5$)—CH$_2$NH]—}

(ab) Cyclo{-Suc[1-COO(CH$_2$—C$_6$H$_4$-4-NO$_2$)]-Trp-Phe-[(R)NH—CH(CH$_2$—C$_6$H$_5$)—CH$_2$NH]—}

(ac) Cyclo{-Suc(1-COOH)-Trp-Phe-[(R)—NH—CH(CH$_2$—C$_6$H$_5$)—

(ah) Cyclo{-Suc[1(S)-(morpholin-4-yl)]-Trp-Phe-[(R)—NH—CH(CH$_2$—C$_6$H$_5$)—CH$_2$—NH]—}trifluoroacetic acid (ai) Cyclo{-Suc[1(S)-N(CH$_3$)$_2$]-Trp-Phe-[(R)—NH—CH(CH$_2$—C$_6$H$_5$)—CH$_2$—NH]—}trifluoroacetic acid (aj) Cyclo{-Suc[1(S)-(piperidin-4-yl)]-Trp-Phe-[(R)—NH—CH(CH$_2$—C$_6$H$_5$)—CH$_2$—NH]—}trifluoroacetic acid (ak) Cyclo{-Suc[1(S)—(N(CH$_2$CH$_2$OH)$_2$)]-Trp-Phe-[(R)—NH—CH(CH$_2$—C$_5$H$_5$)—CH$_2$—NH]}trifluoroacetic acid (al) Cyclo{-Suc[1(S)—(N(CH$_2$CH(OH)CH$_2$OH)]-Trp-Phe-[(R)—NH—CH(CH$_2$—C$_6$H$_5$)—CH$_2$—NH]—}trifluoroacetic acid (am) Cyclo{-Suc[1(S)-(3-carboxypropanoyl)amino]-Trp-Phe-[(R)—NH—CH(CH$_2$—C$_6$H$_5$)—CH$_2$—NH]—}

(an) Cyclo{-Suc[1(S)-[3-N'-β-D-glucopyranos-1-yl)-carboxamidopropanoyl]amino]-Trp-Phe-[(R)NH—CH(CH$_2$—C$_6$H$_5$)—CH$_2$NH]—}

(ao) Cyclo{-Suc[1(S)-[(carboxymethyl)amino]-Trp-Phe-[(R)—NH—CH(CH$_2$—C$_6$H$_5$)—CH$_2$—NH]—}trifluoroacetic acid (ap) Cyclo{-Suc[1(S)-[N'-β-D-glucopyranos-1-yl)-carboxyamideomethyl]amino]-Trp-Phe-[(R)—NH—CH(CH$_2$—C$_6$H$_5$)—CH$_2$—NH]—}trifluoroacetic acid (aq) Cyclo{-Suc[1(S)-(quinyl)amine]-Trp-Phe-[(R)—NH—CH(CH$_2$—C$_6$H$_5$)—CH$_2$—NH]—}

(ar) Cyclo{-Suc[1(S)-(4-aminobutanoyl)amino]-Trp-Phe-[(R)—NH—CH(CH$_2$—C$_6$H$_5$)—CH$_2$—NH]—}trifluoroacetic acid (as) Cyclo{-Suc[1(S)-(1,4')bipiperidin-1-yl]acetamido]-Trp-Phe-[(R)—NH—CH(CH$_2$—C$_6$H$_5$)—CH$_2$—NH]—}trifluoroacetic acid (at) Cyclo{-Suc[1-N-(β-D-glucopyranos-1-yl)-carboxyamido]-Trp-Phe-[(R)—NH—CH(CH$_2$—C$_6$H$_5$)—CH$_2$—NH]—}

(au) Cyclo{-Suc[1(S)-(N'-(2-N-acetyl-β-D-glucopyranos-1-yl)-carboxyamido]-Trp-Phe-[(R)—NH—CH(CH$_2$—C$_6$H$_5$)—CH$_2$—NH]—}.

3. A composition comprising a compound of formula (I) according to claim 1 in combination with a suitable carrier or excipient.

4. Compositions according to claim 3, to be used as tachykinin antagonists.

5. Compositions according to claim 4, to be used as antagonists of the human NK-2 receptor.

6. A method of inhibiting bronchoconstriction comprising administering a compound according to claim 1 for a time and under conditions effective to antagonize NK-2 (neurokinin-2) receptors.

7. A method of inhibiting bronchoconstriction comprising administering a compound according to claim 1 to a mammal afflicted with asthma for a time and under conditions effective to antagonize NK-2 receptors.

8. A method of inhibiting bronchoconstriction comprising administering a compound according to claim 1 to a mammal afflicted with an anxiety disorder for a time and under conditions effective to antagonize NK-2 receptors.

9. A method of inhibiting bronchoconstriction comprising administering quantities of between 0.02 and 10 mg/kg of body weight of active principle consisting of a compound according to claim 1, to a patient afflicted with asthma, coughing, pulmonary irritation, intestinal spasms, spasms of the biliary tract, local spasms of the bladder and of the ureter during cystitis or kidney infections and colics for a time and under conditions effective to antagonize NK-2 receptors.

10. A mixture comprising two or more compounds according to claim 1.

11. A method of inhibiting bronchoconstriction comprising administering a compound according to claim 1 for a time and under conditions effective to antagonize NK-2 receptors.

12. A method of inhibiting bronchoconstriction comprising administering a compound according to claim 1 to a mammal in need thereof for a time and under conditions effective to antagonize NK-2 receptors.

13. A method according to claim 12 wherein said mammal is afflicted with a disorder selected from the group consisting of the bronchospastic and inflammatory component of asthma, coughing, pulmonary irritation, intestinal spasms, spasms of the biliary tract, local spasms of the bladder and of the ureter during cystitis, and kidney infections and colics.

* * * * *